United States Patent [19]

Mendelsohn et al.

[11] Patent Number: 4,943,533
[45] Date of Patent: Jul. 24, 1990

[54] HYBRID CELL LINES THAT PRODUCE MONOCLONAL ANTIBODIES TO EPIDERMAL GROWTH FACTOR RECEPTOR

[75] Inventors: John Mendelsohn, La Jolla, Calif.; Tomoyuki Kawamoto, Hiroshima, Japan; Gordon Sato, Lake Placid, N.Y.; J. Denry Sato, Duarte, Calif.

[73] Assignee: The Regents of the University of California, Berkeley, Calif.

[21] Appl. No.: 23,988

[22] Filed: Mar. 9, 1987

Related U.S. Application Data

[63] Continuation of Ser. No. 585,300, Mar. 1, 1984, abandoned.

[51] Int. Cl.$^5$ .......................... C12N 5/00; C12R 1/91; C07K 15/12; A61K 39/395
[52] U.S. Cl. .............................. 435/240.27; 435/948; 530/387; 424/85.8
[58] Field of Search ................. 435/7, 68, 172.2, 948, 435/240.27, 240.25; 436/548; 424/85; 530/387

[56] References Cited

PUBLICATIONS

Cohen et al., "Epidermal Growth Factor–Receptor–Protein Kinase Interactions", *J. Biol. Chem.*, vol. 255, no. 10; 1980; pp. 4834–4842.
Grimm et al., "Immunoprecipitation of the EGF Receptor Using Hybridoma Antibodies"; *J. Supramol. Structure;* vol. 9 (Suppl. 4), Abstract 437; 1980; p. 167.
Schreiber et al.; "Monoclonal Antibodies Against Receptor for Epidermal Growth Factor Induce Early and Delayed Effects of Epidermal"Growth Factor; *PNAS*, vol. 78, no. 12, Dec. 1981, pp. 7535–7539.
Sato et al., "Biological Effects in Vitro of Monoclonal Antibodies to Human Epidermal Growth Factor Receptors"; *Mol. Biol. Med.*, vol. 1, no. 15; Aug. 1983; pp. 511–529.
Beheadian et al.; "Isolation of a Variant of A431 Cells Using a Ricin A–Conjugated Monoclonal Antibody Directed to EGF Receptors", *J. Cell Biology*, vol. 97 (5 Part 2), Abstract #1540, Aug., 1983; p. 408a.
Waterfield et al., "A Monoclonal Antibody to the Human Epidermal Growth Factor Receptor"; *J. Cellular Biochem.*, vol. 20; 1982; pp. 149–161.
Schreiber et al., "Biological Role of Epidermal Growth Factor–Receptor Clustering"; *J. Biol. Chem., vol. 258, no. 2, Jan. 25, 1983; pp. 846–853.*
Grimm et al., "Hybridoma Antibodies to A431 Cell Plasma Membranes: Tests for Specific Immunoprecipitation of EGF Receptors", in *Monoclonal Antibodies in Endocrine Research* Raven Press, New York Eisenbarth (Ed.), 1981 pp. 99–110.
Gooi et al., "The Carbohydrate Specificities of the Monoclonal Antibodies 29.1, 455 and 3C1B12 to the Epidermal Growth Factor Receptor of A431 Cells." *Bioscience Reports.* 1985. vol. 5, pp. 83–94.
Masui et al. "Growth Inhibition of Human Tumor Cells in Athymic Mice by Anti–Epidermal Growth Factor Receptor Monoclonal Antibodies." *Cancer Research.* Mar. 1984. vol. 44, pp. 1002–1007.
Kawamoto, Tomoyuki, et al., "Growth Stimulation of A431 Cells by Epidermal Growth Factor: Identification of High–Affinity Receptors for Epidermal Growth Factor By an Anti–Receptor Monoclonal Antibody." *Proceedings of the National Academy of Sciences,* U.S.A., Mar. 1983, 80:1337–1341.
Cohen, Stanley, et al., "Epidermal Growth Factor–Receptor–Protein Kinase Interactions." *The Journal of Biological Chemistry.* May 25, 1980; vol. 255, no. 10: 4834–4842.
Linsley, Peter S., and C. Fred Fox. "Direct Linkage of EGF to Its Receptor: Characterization and Biological Relevance." *Journal of Supramolecular Structure.* 1980, 14:441–459.

Primary Examiner—Elizabeth C. Weimar
Attorney, Agent, or Firm—Brown, Martin, Haller & McClain

[57] ABSTRACT

Hybrid cell lines that synthesize and secrete monoclonal antibodies against epidermal growth factor receptor generated by the fusion of myeloma cells to lymphocytes immunized with epidermal growth factor receptor are disclosed. The method of generating the hybridomas, as well as therapeutic and diagnostic uses of the monoclonal antibodies in both cancer treatment and research are also disclosed.

8 Claims, 4 Drawing Sheets

HYBRID CELL LINES THAT PRODUCE MONOCLONAL ANTIBODIES TO EPIDERMAL GROWTH FACTOR RECEPTOR

This is a continuation of application Ser. No. 585,300 filed Mar. 1, 1984, now abandoned.

FIELD OF THE INVENTION

This invention relates to hybrid cell lines that produce monoclonal antibodies to epidermal growth factor receptor, to uses of the monoclonal antibodies in cancer therapy and diagnosis, and methods of producing the same.

BACKGROUND OF THE INVENTION

There have been many attempts at passive immunotherapy of malignant tumors, but there are only a few reports in which the administration of conventional antisera inhibited tumor growth in experimental animals or in cancer patients (see Rosenberg and Terry, Advances in Cancer Research, Vol. 25, pp. 323-388 [1977]). In most of these studies antibodies against tumor-associated antigens have been used for treatment with little success. The major reasons are the difficulties in identifying tumor-associated antigens and in preparing homogeneous antibody in large quantities by conventional methods. Development of the hybridoma technique by Kohler and Milstein (Nature, Vol. 256, pp.495-497 [1975]), coupled with the realization that cell surface antigens other than tumor-associated antigens may play a role in regulating tumor cell growth, has led to a renewed interest in experimental cancer immunotherapy centered around the use of monoclonal antibodies. Considerable effort has been, and continues to be directed towards making monoclonal antibodies against plasma membrane receptors for growth factors. It is well known that the proliferation of tumor cells is controlled by various growth factors, and it has been suggested that monoclonal antibodies against growth factor receptors, which could block access of growth factors to the receptors, might provide useful therapeutic agents. Recently Trowbridge and Domingo reported in Nature, Vol. 294, pp. 171-173 (1983), that treatment with anti-transferrin receptor monoclonal antibody inhibits tumor formation by a human melanoma cell line in athymic mice. Furthermore, monoclonal antibodies against other receptors for growth factors have been derived. With regard to the present invention it is important to note that while some data have been published on monoclonal antibodies to epidermal growth factor receptor, to date there have been no reports showing that monoclonal antibodies to epidermal growth factor receptor inhibit tumor cell growth in vivo or in vitro.

SUMMARY OF INVENTION

According to this invention hybridoma cell lines are generated that synthesize and secrete monoclonal antibodies that bind to different epitopes on epidermal growth factor receptor. The binding of such monoclonal antibodies to certain types of human tumor cells inhibits their growth, and thus may be of considerable therapeutic use. Also such monoclonal antibodies may be of diagnostic value in detecting certain types of tumors.

BRIEF DESCRIPTION OF DRAWINGS

Table I. Shows the apparent dissociation constants and number of binding sites of epidermal growth factor and monoclonal antibodies to A-431, HeLa and human fibroblast cells.

Table II. Shows the effect of monoclonal antibodies 528, 225, 579 and 455 on the phosphorylation of A-431 membranes in the presence and absence of epidermal growth factor (EGF). Also the table shows the results obtained in the absence or presence of normal mouse immunoglobulin.

Table III. Shows the inhibition of tumor formation by A-431 cells in animals treated with monoclonal antibodies 528, 225 and 455.

Table IV. Shows the growth inhibition of human tumor cells in athymic mice by the monoclonal antibody 528.

DETAILED DESCRIPTION OF SPECIFIC EMBODIMENT

The following terms are used throughout the subsequent discussion and are herein defined for easy reference. "Epidermal growth factor receptor" is understood to mean a glycoprotein with an apparent molecular weight of about 165,000 to which the mitogen epidermal growth factor binds to effect cell growth. "Epidermoid carcinoma cells" is understood to mean cancer cells derived from the outermost layer of the skin. "Myeloma cell line" is understood in encompass one of many well-known cancerous murine cell lines of lymphoid origin that have been adapted for use as fusion partners to immortalize normal B-cell lymphocytes. "Non-ionic detergent" is understood to mean detergents that do not ionize in solution, e.g., Triton-X 100 and NP-40.

In accordance with the invention lymphocytes are immunized with epidermal growth factor receptor derived from tumor cells, and these lymphocytes are employed to ( generate hybridomas by fusion to myeloma cell lines. Hybridomas generated in this manner by the method of Kohler and Milstein (Nature, Vol. 256, pp.

495–497 [1975]), as modified by Galfre et al (Nature, Vol. 266, pp. 550–552 [1977]), secrete monoclonal antibodies that inhibit the growth of tumor cells. By this technique monoclonal antibodies can be generated that bind to different regions on the epidermal growth factor receptor. These monoclonal antibodies fall into two broad classes: those that compete with epidermal growth factor for binding to the receptor, and those that do not. Both types of monoclonal antibodies inhibit tumor cell growth in athymic mice.

Partially purified epidermal growth factor receptors were obtained from human tumor cells such as the human epidermoid carcinoma cell line, A-431. Epidermal growth factor receptors from these cells were used to immunize laboratory animals. Purification of the receptors was effected by solubilization of A-431 membranes in a non-ionic detergent followed by affinity chromatography to epidermal growth factor covalently linked to a solid support matrix, specifically Affi-Gel beads, as described by Cohen et al., Journal of Biological Chemistry, Vol. 255, pp. 4834–4842 (1980). The A-431 epidermal growth factor receptor was then eluted from the beads by incubation at high pH. This material was used to intravenously immunize laboratory animals such as mice. A typical immunization program entailed three intravenous immunizations with ten micrograms of epidermal growth factor receptor at two week intervals, as described by Kawamoto et al., Proceedings of the National Academy of Sciences, Vol. 80, pp. 1337–1341 (1983). A subsequent intraperitoneal injection of paraformaldehyde fixed A-431 cells was given four days prior to removing the spleens. Splenocytes were isolated from the spleens and fused to one of several routinely used myeloma cell lines (P3-X63-Ag8-653, NS-1-Ag4 1, etc.) by standard techniques using polyethylene glycol 1500 by Galfre's method described in Nature, Vol. 266, pp. 550–552 (1977). The resultant hybridomas were screened for the ability to secrete monoclonal antibodies against epidermal growth factor receptor by an indirect binding, or a binding inhibition assay, as described by Kawamoto et al., Proceedings of the National Academy of Sciences U.S.A., Vol. 80, pp. 1337–1341 (1983).

Two types of monoclonal antibodies are produced by the techniques used in this invention: one type competes with epidermal growth factor for binding to the epidermal growth factor receptor; the other binds to the receptor but does not compete with epidermal growth factor for binding. Both types of monoclonal antibodies inhibit tumor cell growth in vivo, although only the former do so in our present in vitro studies. Additionally, these monoclonal antibodies may be attached to substances such as radioactive, bioluminescent, or chemiluminescent labels, or physiologically active agents that disrupt or interfere with normal cell growth.

The hybrid cell lines described in this invention are on deposit with the American Type Culture Collection (ATCC), 12301 Parklawn, Md. 20852. The ATCC deposit numbers are HB8506, HB8507, HB8508 and HB8509.

This invention was made with government support under Grant Nos. CA33397, CA09290, CA23052, and GM17702, awarded by the National Institutes of Health, Department of Health and Human Services. The government has certain rights in this invention.

EXAMPLE 1

MONOCLONAL ANTIBODY 528 AGAINST EPIDERMAL GROWTH FACTOR RECEPTOR.

Preparation of epidermal growth factor receptor.

Epidermal growth factor receptors from the human epidermoid carcinoma cell line, A-431, were partially purified as described by Cohen et al., Journal of Biological Chemistry, Vol. 255, pp. 4834–4842 (1980), and used to immunize Balb/c mice. A-431 cells were obtained from Dr. George Todaro via Dr. Tony Hunter and have been described by Dr. Todaro in the Proceedings of the National Academy of Sciences U. S. A, Vol. 74, pp. 565–569. Purification of the receptor was effected by solubilizing 400 micrograms of A-431 membrane protein in 200 microliters of 20 mM Hepes buffer at pH 7.4, containing 1% Triton X-100 and 10% glycerol. The suspension was allowed to stand at room temperature for 20 minutes and the mixture centrifuged at 100,000 Xg for 60 minutes at 4° C. After centrifugation, 150 microliters of the soluble A-431 membrane suspension were affinity chromatographed to 150 microliters of Affi-Gel beads containing covalently attached mouse epidermal growth factor. The mixture was stirred in a 1 ml Eppendorf microtest tube for 30 minutes at room temperature. The beads were centrifuged for 1 minute and the pelleted gel washed three times with 1 ml of cold buffer containing 10% glycerol, 1% Triton X-100, adjusted to pH 7.2 with NaOH. Lastly, A-431 epidermal growth factor receptor was eluted off the beads by adding 150 microliters of elution buffer containing 10% glycerol, 1% Triton X-100, 5 mM ethanolamine, at a final pH 9.7. The mixture was stirred for 30 minutes and the beads separated from epidermal growth factor receptor by centrifugation.

Immunization procedure.

The A-431 epidermal growth factor receptors eluted off the Affi-Gel beads were used to immunize mice. Balb/c mice were immunized intravenously three or four times at two-week intervals with approximately 10 micrograms of A-431 epidermal growth factor receptor. One month after the last immunization mice were given an intraperitoneal boost of $1-5 \times 10^6$ A-431 cells fixed with 0.2% paraformaldehyde in phosphate buffered saline.

Preparation of cell fusion partners: splenocytes and myeloma cells.

Four days after mice were injected intraperitoneally with A-431 cells, their spleens were removed and the splenocytes were isolated. This was done by teasing the spleens apart in Dulbecco's Modified Eagle's medium, and separating the splenocytes from tissue debris by letting the latter sediment under unit gravity for several minutes The splenocytes were collected and washed three times with Dulbecco's Modified Eagle's medium. The mouse myeloma cell line, NS-1-Ag4-1, was maintained at 37° in a humidified atmosphere of 7.5% $CO_2$ and 92.5% air in a medium consisting of 1 or 10% fetal calf serum in a 1:1 (volume/volume) mixture of Dulbecco's Modified Eagle's and Ham's F12 media, supplemented with 10 micrograms/ml bovine insulin, 10 micrograms/ml human transferrin, 10 micromolar ethanolamine, $1 \times 10^{-9}$ M sodium selenite, and 10 micromolar 2-mercaptoethanol. The media also contained 15 mM Hepes, pH 7.6, 2.0g/L sodium bicarbonate, 40mg/L penicillin, 8mg/L ampicillin, 90mg/L streptomycin.

Fusion procedure.

Hybridomas were produced by fusing the mouse spleen cells to the myeloma cell line NS-1-Ag4-1 according to Galfre et al. Nature, Volume 266, pp. 550-552 (1977). This consists of incubating a cell pellet composed of splenocytes and myeloma cells in a 10:1 ratio in the presence of 1 ml of Dulbecco's Modified Eagle's medium without serum containing 50% polyethylene glycol 1500 for 1 minute at 37° C. Following this incubation 20 mls of Dulbecco's Modified Eagle's medium was gently added over a period of 5 minutes and then the mixture of cells centrifuged for 5 minutes at 200xg. The cell pellet was gently resuspended and washed two times. Finally the cells were resuspended in Dulbecco's Modified Eagle's culture media containing 20% fetal calf serum and hypoxanthine, aminopterin and thymidine (HAT), as described by Littlefield, Science, Vol 145, p. 709. Cells were plated at various cell densities in 96-well microtiter plates containing spleen cell feeder layers as described by Kawamoto et al, Analytical Biochemistry, Vol. 130, pp. 445-453 (1983). Since the myeloma cell lines are resistant to 8-azaguanine they lack the enzymes thymidine, kinase or hypoxanthine guanine phosphoribosyl transferase Consequently, unfused myeloma cells die in HAT media Hybridomas, however, survive and grow since the enzymes necessary for survival in HAT are derived from the spleen cells.

Identification of hybridoma 528 that secretes monoclonal antibody against A-431 epidermal growth factor receptor.

Hybridoma 528 that secretes monoclonal antibodies that bind to A-431 epidermal growth factor receptor was identified approximately two weeks after fusion by assaying tissue culture medium from microtiter wells that exhibited hybridoma growth. A 125I-epidermal growth factor binding inhibition assay was used to screen tissue culture supernatants for monoclonal antibodies against epidermal growth factor receptor, as described by Kawamoto et al, Proceedings of the National Academy of Sciences, Vol. 80, pp. 1337-1341 (1983). This assay tells the investigator not only that the culture media contains monoclonal antibodies against epidermal growth factor receptor but also whether the monoclonal antibody competes with epidermal growth factor for binding to the epidermal growth factor receptor. The assay was conducted by adding $2 \times 10^4$ paraformaldehyde fixed A-431 cells onto glass fiber filters in punctured microtiter wells. The cells were washed two times with 0.25% gelatin and 5% newborn calf serum in phosphate buffered saline, and then incubated for 2.5 hours at 37° C. in 50 microliters of a 1:1 mixture of Dulbecco's Modified Eagle's medium/Ham's F12 medium with 100 picograms $125_I$-epidermal growth factor ($1.5 \times 10^6$ cpm/nanogram) and increasing concentrations of the monoclonal antibody. Receptor grade epidermal growth factor was labelled with $125_I$ by the chloramine T method as described by Hunter et al., Nature, Vol. 194, pp.495-496 (1962). The cells were washed and filter-bound radioactivity was measured with a gamma counter. Utilizing this assay the hybridoma that secretes the monoclonal antibody 528 was detected because of its capacity to compete with $125_I$-epidermal growth factor for binding to the receptor.

Hybridoma 528 was cloned by standard techniques and purified monoclonal antibody from the hybridoma was prepared and used to conduct a variety of studies. Monoclonal antibody 528 was purified from either tissue culture media conditioned by hybridoma 528 or ascites fluid produced in BALB/c mice. This material was fractionated on a diethylaminoethyl-cellulose column at 4° C. The flow through fraction was adjusted to pH 8.0 and it was subsequently passed over a 5ml column of protein A-agarose at 4° C. Bound antibody was eluted with a solution containing 1 M acetic acid (pH 3.0), 100 mM glycine, and 20 mM sodium chloride, and the eluate was dialyzed extensively against a 1:1 mixture of Dulbecco's Modified Eagle's Ham's F12 culture media. Aliquots of antibody were sterilized by filtration, frozen and stored at −20° C. Monoclonal antibody 528 Fab fragments were prepared as described by Garvey et al., Methods in Immunology, 3rd edition, Addison-Wesley Publishing Co., New York, pp. 256-266 (1977). The subclass of the 528 monoclonal antibody was determined with goat anti mouse IgG subclass sera on double diffusion plates as described by Ouchterlony, Progress in Allergy, Vol. 5 (P. Kallos, ed) Karger, Basal, pp. 1-78 (1958), and found to be IgG2a.

Properties of purified 528 monoclonal antibody.

A. Competitive binding of monoclonal antibody 528 to A-431 cell. Purified 528 monoclonal antibodies were assayed for their ability to inhibit the binding of $125_I$-epidermal growth factor to A-431 cells fixed with paraformaldehyde (FIG. 1). 528 monoclonal antibody maximally blocked the binding of 0.33 Nm $125_I$-epidermal growth factor by 97%. The binding of $125_I$-epidermal growth factor in the presence of excess unlabelled epidermal growth factor was less than 5% of the binding in the absence of unlabelled epidermal growth factor. Similar levels of inhibition were achieved when the concentration of $125_I$-epidermal growth factor was increased to 20 nM. 528 monoclonal antibody effectively blocked the binding of monoclonal antibodies that compete with epidermal growth factor for binding to epidermal growth factor receptors on A-431 cells. 280 nM epidermal growth factor inhibited the binding of trace amounts of $125_I$-labelled 528 by at least 75%.

B. Saturation binding of 528 monoclonal antibodies to A-431, HeLa and human fibroblasts cells. 528 monoclonal antibodies bound in a specific and saturable manner to paraformaldehyde-fixed A-431 cells, HeLa cells and human foreskin fibroblasts. Scatchard analysis of binding data are summarized in Table I. 528 monoclonal antibodies bound to a single class of receptor sites on all three cell types with apparent dissociation constants (Kd ) of $1.2-2.5 \times 10^{-9}$M. The number of antibody binding sites for A-431 cells varied from $1.2-2.2 \times 10^6$/cell. In contrast there were approximately 100-fold fewer binding sites per cell for HeLa and human fibroblasts.

C. Immunoprecipitation of epidermal growth factor receptor by monoclonal antibody 528. Purified 528 monoclonal antibodies covalently attached to Affi-Gel 10 were used to immunoprecipitate epidermal growth factor receptors from A-431 membranes solubilized with Triton X-100. Membranes were prepared from confluent cultures of A-431 cells by hypotonic shock according to the method of Thom, et al., Biochemical Journal, Vol. 168, pp. 187-194 (1977). About 50 micrograms of A-431 membrane protein were incubated for 16 hours at 4° C., and the precipitates were collected by centrifugation. The immunoprecipitates were washed 5 times with buffer containing 0.5% Triton X-100, 0.1% sodium dodecyl sulfate (SDS), 20mM HEPES and 10% glycerol, and bound protein was eluted in boiling SDS gel electrophoresis sample buffer. This material was subject to electrophoresis under reducing conditions in a 7.5% SDS-polyacrylamide gel and proteins detected with silver stain. Monoclonal antibody 528 precipitated polypeptides of molecular weights 165,000 and 45,000. These molecular weights are characteristic of the intact A-431 epidermal growth factor receptor and a degradation product of the receptor generated by a calcium-dependent protease as described by Cohen et al., Journal of Biological Chemistry, Vol. 257, pp. 1523–1531 (1982), and Cassel and Glaser, Journal of Biological Chemistry, Vol. 257, pp. 9845–9848.

D. Effect of 528 monoclonal antibodies on epidermal growth factor-stimulated phosphorylation of A-431 membrane proteins Epidermal growth factor has been shown to enhance the phosphorylation of A-431 membrane proteins. To test the effect of epidermal growth factor receptor monoclonal antibody 528 on this event, A-431 membranes were prepared from $1 \times 10^8$ A-431 cells and resuspended in 500 microliters of 20mM Hepes buffer, pH 7.4, containing 1 mM magnesium chloride 20 microliter aliquots of A-431 membranes were incubated at 0° C. for 10 minutes with or without 20 nM epidermal growth factor in the presence or absence of 1 micromolar of 528 monoclonal antibody in a total volume of 200 microliters of 20mM Hepes, pH 7.4, 1 mM magnesium chloride. 12 uCi of [$\gamma$-32P]ATP were added to the reaction and the mixture incubated for a further 10 minutes at 0° C. 100 micrograms of bovine serum albumin (BSA) in 50 microliters phosphate buffered saline were added, and the phosphorylation reaction stopped by the addition of 150 microliters of ice cold 50% trichloroacetic acid containing 10 millimolars sodium pyrophosphate. The membranes were collected by centrifugation in a microfuge, washed three times with 10% trichloroacetic acid, solubilized in 20 microliters of 0.3 N sodium hydroxide, and neutralized with 0.3N hydrochloric acid. Incorporated radioactivity was measured by liquid scintillation in a scintillation counter. Table II summarizes the results of an experiment designed to test the effects of 528 monoclonal antibodies on the epidermal growth factor stimulated protein kinase activity of intact A-431 membranes. The addition of 20 nM epidermal growth factor alone to the phosphorylation reaction results in a two-fold increase in trichloroacetic acid-precipitable radio-activity. 528 monoclonal antibodies at 1 micromolar do not mimic epidermal growth factor in stimulating kinase activity, however, the effect of epidermal growth factor was abolished by 1 micromolar 523 monoclonal antibody.

E. Growth inhibition of human tumors in athymic mice by monoclonal antibody 528.

1. Effect on A-431 tumors. $1 \times 10^7$ A-431 cells were inoculated subcutaneously, in 0.5 ml of phosphate buffered saline, into athymic mice, and the animals treated simultaneously with various amounts of purified 528 monoclonal antibody Subsequent injections of 528 monoclonal antibody were given intraperitoneally either two or three times per week. Sixteen days later the number of mice that developed tumors and the tumor size were noted. Table III shows that monoclonal antibody 528 dramatically inhibits tumor formation. Of six mice administered doses of 0.2 and 2.0 mg of 528 monoclonal antibody none developed tumors.

2. Effect on other types of human tumors. The ability of the monoclonal antibody 528 to inhibit the growth of other types of tumors was tested. Table IV shows that monoclonal antibody 528 inhibits the growth of human lung epidermoid carcinoma cells, T222. Monoclonal antibody 528 does not inhibit the growth of all types of tumors, as it does not inhibit human hepatoma generated from the Li-7 cell line, or HeLa cell derived tumors. The T222 line was established from a tumor removed during surgery, and Li-7 was originally established in Japan by Hiroshashi et al., Cancer Research, Vol. 39, pp. 1819–1829 (1979). Other data demonstrate anti-tumor effects of this antibody upon growth of a variety of epidermoid malignancies.

Figure 2:
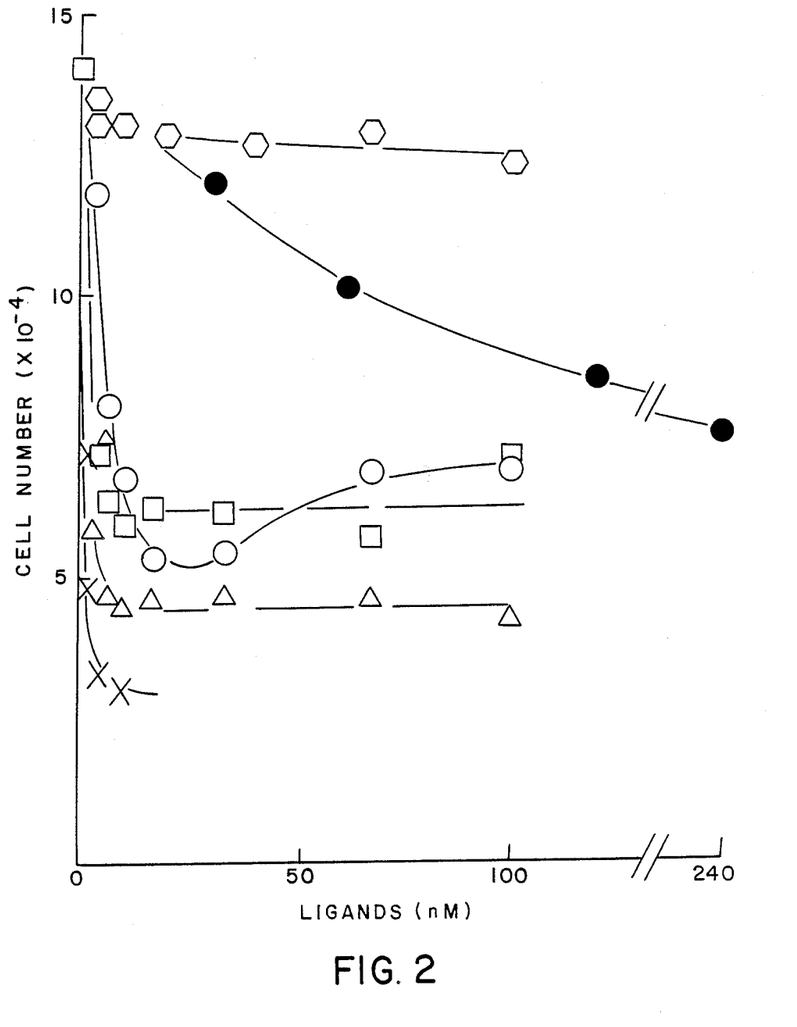
FIG. 2. Effects of monoclonal antibodies on A-431 cell growth. A-431 cells were incubated with monoclonal antibodies 528( ○ ) or 528 Fab fragments (●), 225(△), 579(□), 455( ) or epidermal growth factor(X). Each point represents the mean of duplicate cell counts.
Figure 3:
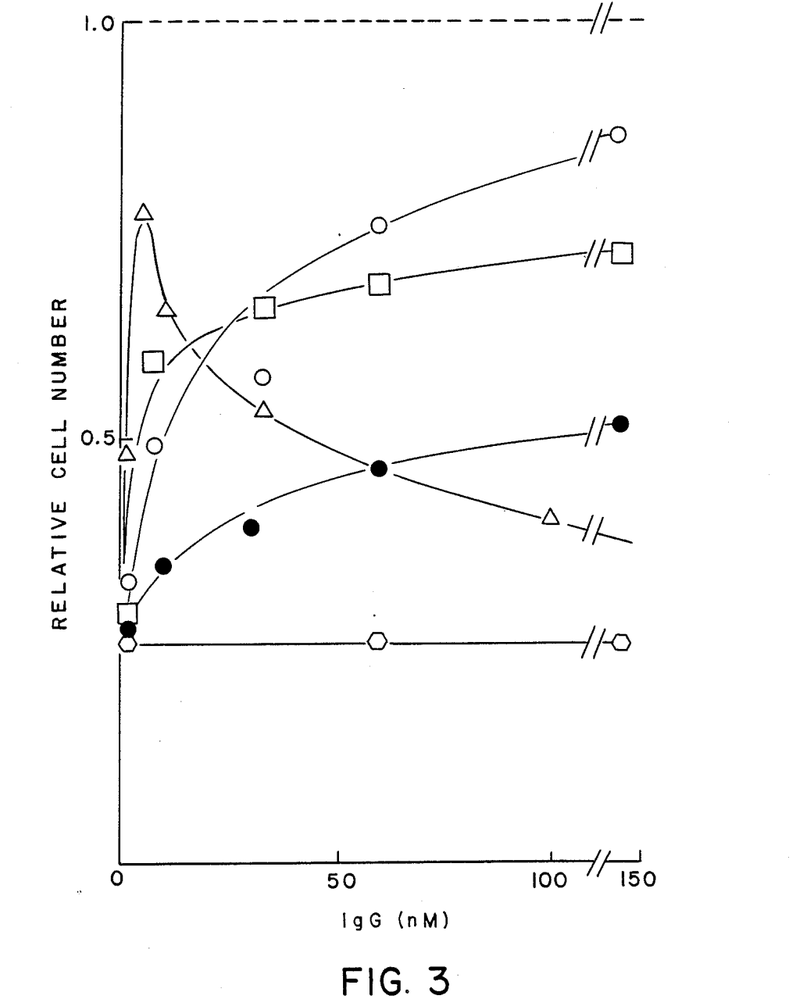
FIG. 3. Effects of monoclonal antibodies on A-431 cell growth in the presence of epidermal growth factor(3 nM). Various concentrations of monoclonal antibodies 528( ○ ) or 528 Fab fragments(●), 225(△), 579(□), or 455( ◯ ) were tested.
Figure 4:
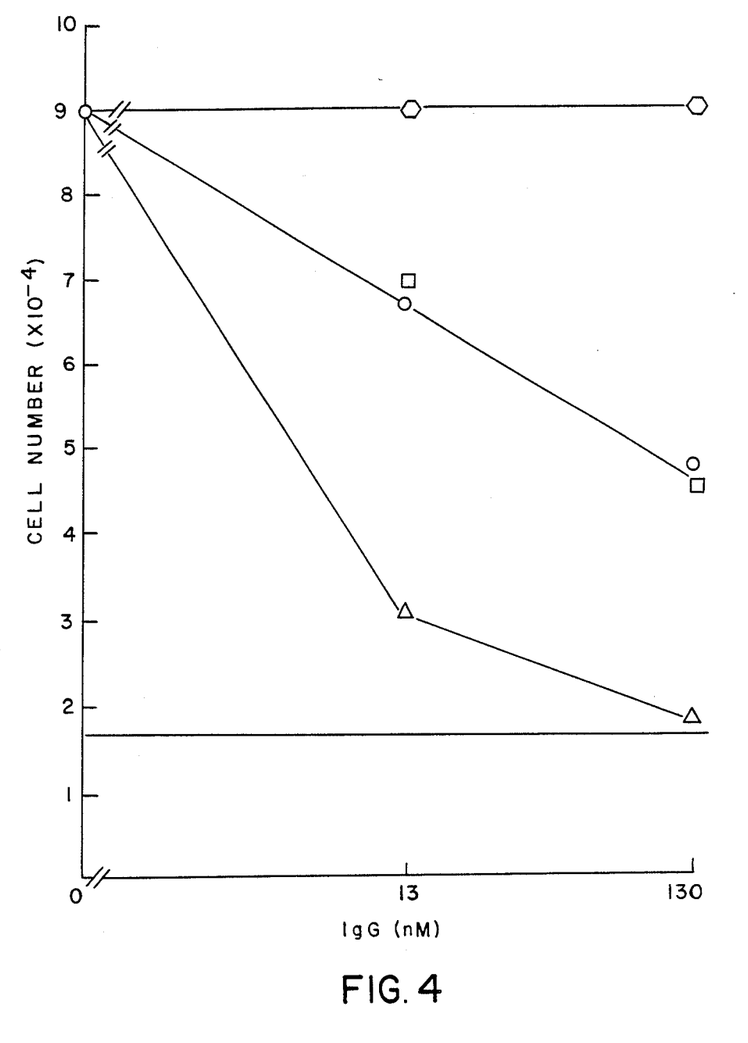
FIG. 4. Effects of monoclonal antibodies on epidermal growth factor induced proliferation of human foreskin fibroblasts. Human foreskin fibroblasts were incubated with monoclonal antibodies 528( ○ ), 225(△), 579(□), or 455(◯) in the presence of 3 nM epidermal growth factor. Cell growth in the presence of no additions or 3 nM epidermal growth factor alone is indicated by the open and closed arrowheads, respectively. Cell growth in the presence of monoclonal antibodies without epidermal growth factor was the same as that in serum-free medium alone.

F. Effect of monoclonal antibody 528 on the growth of A-431 cells and human fibroblasts in vitro. Monoclonal antibody 528 and its Fab fragment inhibit the growth of A-431 cells in vitro (FIG. 2). This effect is not due to the displacement of epidermal growth factor from epidermal growth factor receptors as it was observed in media without epidermal growth factor. In contrast to its inhibitory effects on A-431 cell growth in the absence of epidermal growth factor, certain concentrations of 528 monoclonal antibody may have a stimulatory effect when assayed in the presence of 3 nM epidermal growth factor (FIG. 3). This effect is presently not understood since the monoclonal antibody alone inhibits A-431 growth as does epidermal growth factor at this concentration. The effect of monoclonal antibody 528 on fibroblast growth was studied. In the absence of epidermal growth factor it had no effect. In the presence of 3 nM epidermal growth factor monoclonal antibody 528 significantly inhibits fibroblast growth (FIG. 4). The hybridoma that secretes the monoclonal antibody 528 is on deposit with the American Type Culture collection under the designation HB8509, and the monoclonal antibodies secreted by the hybridoma is similarly on deposit under the designation HB8509.

EXAMPLE 2

MONOCLONAL ANTIBODY 225

The methods used to establish, detect, and characterize the hybridoma that secretes the monoclonal antibody 225 differs slightly from those used in Example 1. The mouse myeloma cell line NS-1-503, a clonal isolate of NS-1-Ag4-1 was used as the fusion partner. NS-1-503, and the hybridoma 225 generated from it, were grown under identical conditions as in Example 1, except that the media was additionally supplemented with 1 mg/ml fatty acid-free bovine serum albumin complexed with oleic acid in a 1:2 molar ratio as described by Kawamoto et al., Analytical Biochemistry, Vol. 130, pp. 445–453 (1983).

Figure 1:
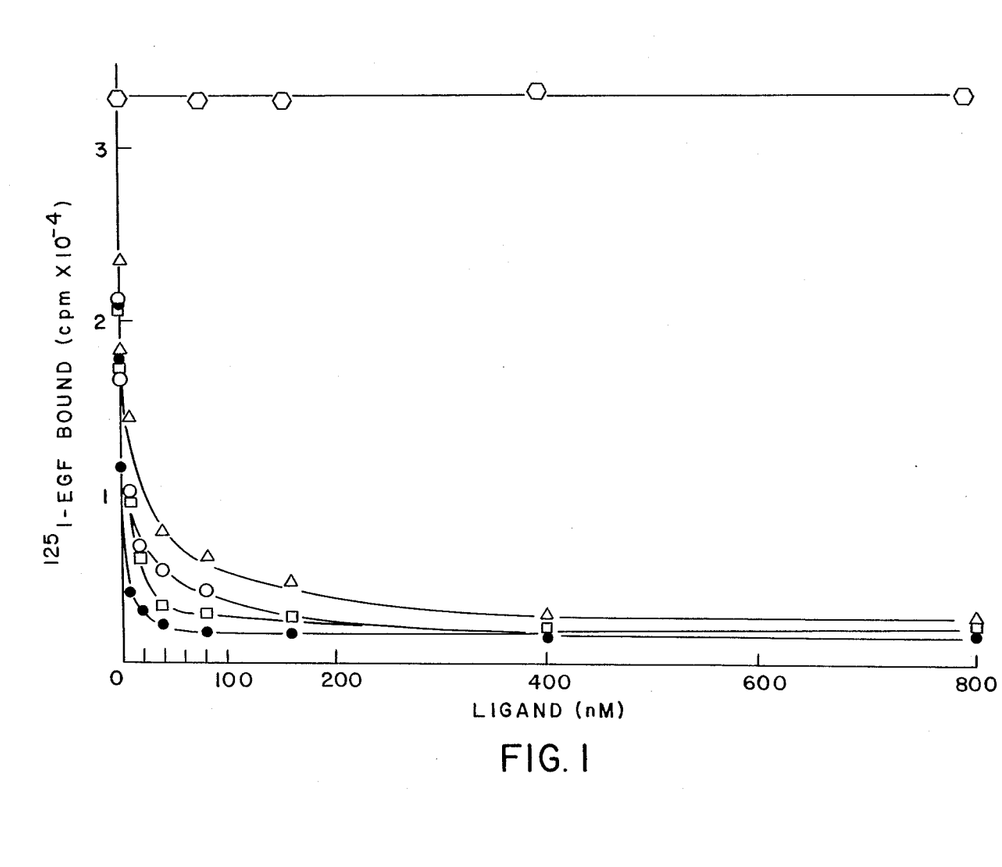
FIG. 1. Shows the inhibition of $125_I$-epidermal growth factor (EGF) binding to A-431 cells by increasing concentrations of monoclonal antibodies 528( ○ ), 225(△), 579( ) and 455(◯) or by EGF(●).

The properties of monoclonal antibody 225 are similar to the monoclonal antibody 528 discussed in Example 1 in most respects (see FIGS. 1–4 and Tables I–IV). In certain respects, however, the properties of monoclonal antibody 225 differ from that it Example 1. First, 225 monoclonal antibody is of the IgG1 subclass. Second, 225 maximally blocked the binding of 0.33 nM 125$_I$-epidermal growth factor by 99% to A-431 cells fixed with paraformaldehyde (FIG. 1). Third, the results of saturation binding of 225 monoconal antibodies to A-431, HeLa and human fibroblasts cells showed that 225 monoclonal antibodies bind to a single class of receptor sites on all three cell types with apparent dissociation constants ($K_d$) of $0.6-1.3\times10^{-9}$M (Table I). The number of binding sites for A-431 cells varied from $0.8-2.2\times10^6$/cell. Fourth, 225 monoclonal antibodies also inhibit the growth of A-431 tumors but are not as good an inhibitor as is the monoclonal antibody 528 in Example 1 (Table III). When an 0.2 mg 2.0 mg dose of monoclonal antibody 225 was administered to five mice, three out of five of the mice developed tumors. Fifth, in the absence of epidermal growth factor, monoclonal antibody 225 inhibits A-431 proliferation in a concentration-dependent manner, the maximum extent of which was 69% (FIG. 2). In the presence of 3 nM epidermal growth factor the proliferative response of A-431 cells as a function of monoclonal antibody 225 concentration differed dramatically from Example 1 (FIG. 3). Maximal stimulation was reached at 5 nM 225 monoclonal antibody with further increases in 225 monoclonal antibody concentration resulting in decreased cell proliferation. Studies on the effects of monoclonal antibody 225 on human fibroblasts proliferation showed that it completely abolished the stimulation of fibroblasts growth due to epidermal growth factor. The hybridoma that secretes the monoclonal antibody 225 is on deposit with the American Type Culture Collection under the designation HB8508, and the monoclonal antibody is similarly on deposit under the designation HB8508.

EXAMPLE 3

MONOCLONAL ANTIBODY 455.

The methods used to establish, detect and characterize the hybridoma that secretes the monoclonal antibody 455 differ slightly from those used in Example 1. First, the mouse myeloma cell line NS-1-503 as described in Example 2 was utilized. Second, an indirect binding assay instead of a binding inhibition assay was utilized to initially detect the monoclonal antibody 455 in tissue culture media. This involved incubating tissue culture media from individual microtiter wells for 2 hours with $2\times10^4$ A-431 cells previously fixed with 0.2% paraformaldehyde, as described by Kawamoto et al. in the Proceedings of the National Academy of Sciences, Vol. 80, pp. 1337-1341 (1983). The presence of monoclonal antibodies in the culture media that bound to A-431 cells was revealed by the subsequent addition of $125_I$-rabbit anti-mouse IgG, and measuring the amount of radiation. Using this assay the hybridoma 455 was detected.

The properties of monoclonal antibodies 455 differ significantly in certain respects from Example 1. First, monoclonal antibody 455 is of the IgG1 subclass. Second, monoclonal antibody 455 has no effect on $125_I$-epidermal growth factor binding to A-431 cells (FIG. 1). Further, monoclonal antibody 455 does not block the binding of monoclonal antibodies that do block $125_I$-epidermal growth factor binding to A-431 cells. Third, monoclonal antibody 455 binds to A-431 cells with a dissociation constant of $2\times10^{-8}$ M (Table I). This is 10-30 fold lower than the affinities of Example 1 or Example 2. Fourth, monoclonal antibody 455 does not block the epidermal growth factor stimulated protein kinase activity associated with A-431 membrane (Table 2). Fifth, at doses of 0.2 and 2.0 mgs of monoclonal antibody 455, three out of five and none out of six mice developed A-431 tumors (Table III). Sixth, in the absence of epidermal growth factor, monoclonal antibody 455 had a marginal inhibitory effect on the growth of A-431 cells (FIG. 2). Similarly, monoclonal antibody 455 in the presence of epidermal growth factor did not stimulate A-431 growth (FIG. 3). Seventh, monoclonal antibody 455 neither stimulated proliferation of human fibroblasts nor inhibited the stimulatory effect of epidermal growth factor in human fibroblasts (FIG. 4). The hybridoma that secretes the monoclonal antibody 455 is on deposit with the American Type Culture Collection under the designation HB8507 and the monoclonal antibody is similarly on deposit under the designation number HB8507.

EXAMPLE 4

MONOCLONAL ANTIBODY 579.

The methods used to establish, detect and characterized the hybridoma that secretes the monoclonal antibody 579 differ slightly from those used in Example 1. First, the mouse myeloma cell line P3-X63-Ag8-653 was used as the fusion partner instead of NS-1-Ag4-1 or NS-1-503. Second, the indirect binding assay described in Example 3 was used to initially detect monoclonal antibody 579 in tissue culture media.

The properties of monoclonal antibody 579 differ slightly from Example 1. First, monoclonal antibody 579 maximally blocks the binding of 0.33 nM $125_I$-epidermal growth factor by 95% to A-431 cells (FIG. 1). Second, monoclonal antibody 579 binds to a single class of receptor sites on A-431 HeLa and human fibroblast cells with apparent dissociation constants of between $0.7-1.8\times10^{-9}$ M (Table I). Third, monoclonal antibody 579 was not tested for its capacity to inhibit tumor growth in vivo, but monoclonal antibody 579 does inhibit tumor cell growth in vitro (FIG. 2). In the absence of epidermal growth factor monoclonal antibody 579 inhibits A-431 cell proliferation in a concentration dependent manner, maximum inhibition being 57% (FIG. 2). In the presence of 3 nM epidermal growth factor, monoclonal antibody 579 can stimulate A-431 cell proliferation but to a slightly lower degree compared to Example 1 (FIG. 3). Studies on the effects of monoclonal antibody 579 at a concentration of 130 nM on human fibroblasts proliferation showed that it reduced the effect of epidermal growth factor stimulation by 50% (FIG. 4). The hybridoma that secretes the monoclonal antibody 579 is on deposit with the American Type Culture Collection under the designation HB8506 and the monoclonal antibody is similarly on deposit under the designation number HB8506.

What is claimed is:

1. Hybridoma 579 that secretes monoclonal antibodies that inhibits epidermoid tumor cell growth, and on deposit with the American Type Culture Collection (ATCC) as CRL HB8506.

2. Hybridoma 455 that secretes monoclonal antibodies that inhibits epidermoid tumor cell growth, and on deposit with the American Type Culture Collection (ATCC) as CRL HB8507.

3. Hybridoma 225 that secretes monoclonal antibodies that inhibits epidermoid tumor cell growth, and on deposit with the American Type Culture Collection (ATCC) as CRL HB8508.

4. Hybridoma 528 that secretes monoclonal antibodies that inhibits epidermoid tumor cell growth and on deposit with the American Type Culture Collection (ATCC) as CRL HB8509.

5. Monoclonal antibodies that inhibit epidermoid tumor cell growth produced from hybridoma 579, on deposit with the American Type Culture Collection (ATCC) as CRL HB8506.

6. Monoclonal antibodies that inhibit epidermoid tumor cell growth produced from hybridoma 455, on deposit with the American Type Culture Collection (ATCC) as CRL HB8507.

7. Monoclonal antibodies that inhibit epidermoid tumor cell growth produced from hybridoma 225, on deposit with the American Type Culture Collection (ATCC) as CRL HB8508.

8. Monoclonal antibodies that inhibit epidermoid tumor cell growth produced from hybridoma 528, on deposit with the American Type Culture Collection (ATCC) as CRL HB8509.

* * * * *